US010571415B2

(12) United States Patent
Shi

(10) Patent No.: US 10,571,415 B2
(45) Date of Patent: Feb. 25, 2020

(54) METHODS AND APPARATUSES FOR EVALUATING CERAMIC MATRIX COMPOSITE COMPONENTS

(71) Applicant: Rolls-Royce Corporation, Indianapolis, IN (US)

(72) Inventor: Jun Shi, Carmel, IN (US)

(73) Assignee: ROLLS-ROYCE CORPORATION, Indianapolis, IN (US)

( * ) Notice: Subject to any disclaimer, the term of this patent is extended or adjusted under 35 U.S.C. 154(b) by 161 days.

(21) Appl. No.: 15/652,910

(22) Filed: Jul. 18, 2017

(65) Prior Publication Data

US 2018/0038813 A1     Feb. 8, 2018

Related U.S. Application Data

(60) Provisional application No. 62/369,780, filed on Aug. 2, 2016.

(51) Int. Cl.
*G01N 22/02*     (2006.01)
*G01N 25/72*     (2006.01)
(Continued)

(52) U.S. Cl.
CPC .............. *G01N 25/72* (2013.01); *G01M 15/14* (2013.01); *G01N 22/02* (2013.01); *G01N 2021/8472* (2013.01)

(58) Field of Classification Search
CPC .................. G01N 25/72; G01N 25/18; G01N 2021/8427; G01N 2021/8438; G01N 2021/8864; G01N 21/35; G01N 21/8851; G01N 2203/0057; G01N 33/388; G01N 2021/8472; G01N 22/02; G01J 5/0088; G01J 2005/0077; G01J 5/0022; G01J 2005/0081; G01K 7/02; G01K 17/06;
(Continued)

(56) References Cited

U.S. PATENT DOCUMENTS 5,111,048 A * 5/1992 Devitt ................... G01N 25/72
                                                        250/341.6
5,567,051 A * 10/1996 Annati ..................... G01N 3/60
                                                         374/15
(Continued)

FOREIGN PATENT DOCUMENTS

JP          61096475 A * 5/1986
JP       403084472 A * 4/1991
(Continued)

OTHER PUBLICATIONS

Smith, C. E., et al., "Electrical Resistance as a Nondestructive Evaluation Technique for SiC/SiC Ceramic Matrix Composites Under Creep-Rupture Loading," *International J. of Appl. Ceram. Technol.*, 8, 2 (2011) pp. 298-307.

*Primary Examiner* — Gail Kaplan Verbitsky
(74) *Attorney, Agent, or Firm* — Brinks Gilson & Lione

(57) ABSTRACT

Methods and apparatuses for evaluating ceramic matrix composite components are provided. In one example, a method for evaluating a ceramic matrix composite (CMC) component includes applying an electrical voltage to the CMC component at conditions to heat and cause a temperature increase in at least a portion of the CMC component. The temperature increase is sensed for detecting a presence of a defect in the CMC component.

13 Claims, 1 Drawing Sheet

(51) Int. Cl.
*G01M 15/14* (2006.01)
*G01N 21/84* (2006.01)

(58) Field of Classification Search
CPC .......... C04B 35/806; C04B 2235/5224; C04B 35/117; C04B 41/87
USPC ...................... 374/4, 5, 57, 45, 46, 144, 153
See application file for complete search history.

(56) References Cited

U.S. PATENT DOCUMENTS

| | | | | |
|---|---|---|---|---|
| 6,123,452 A | * | 9/2000 | Uchimura | G01N 3/60 374/57 |
| 6,575,620 B1 | * | 6/2003 | Banaszak | G01N 3/068 374/4 |
| 6,698,288 B2 | * | 3/2004 | Shirzad | G01N 25/72 250/334 |
| 6,730,912 B2 | * | 5/2004 | Sun | G01N 25/72 250/341.1 |
| 6,906,611 B2 | * | 6/2005 | Schrank | H01C 1/14 338/268 |
| 7,654,734 B2 | * | 2/2010 | Jiang | G01K 7/02 374/102 |
| 8,308,352 B1 | * | 11/2012 | Waldrop, III | G01N 3/60 374/12 |
| 9,085,991 B2 | * | 7/2015 | Golecki | C04B 35/803 |
| 9,701,072 B2 | * | 7/2017 | Corman | B23P 6/045 |
| 10,152,784 B2 | | 12/2018 | Nalladega | G06T 5/50 |
| 2001/0042746 A1 | * | 11/2001 | Tanaka | H05B 3/48 219/541 |
| 2002/0048306 A1 | | 4/2002 | Sauvant et al. | |
| 2002/0158626 A1 | | 10/2002 | Shay et al. | |
| 2003/0021382 A1 | | 1/2003 | Iwanczyk et al. | |
| 2003/0039796 A1 | * | 2/2003 | Ito | H01L 21/67103 428/66.6 |
| 2003/0152186 A1 | | 8/2003 | Jurczyk et al. | |
| 2004/0190377 A1 | | 9/2004 | Lewandowski et al. | |
| 2005/0072236 A1 | | 4/2005 | Heyman et al. | |
| 2005/0169348 A1 | | 8/2005 | Chen et al. | |
| 2006/0004290 A1 | | 1/2006 | Smith et al. | |
| 2006/0080048 A1 | | 4/2006 | Kessler et al. | |
| 2006/0274813 A9 | | 12/2006 | Chen et al. | |
| 2007/0189359 A1 | | 8/2007 | Chen et al. | |
| 2007/0240515 A1 | | 10/2007 | Kessler et al. | |
| 2008/0038477 A1 | | 2/2008 | Stewart et al. | |
| 2008/0223152 A1 | | 9/2008 | Georgeson et al. | |
| 2008/0312846 A1 | | 12/2008 | Kessler et al. | |
| 2009/0312956 A1 | * | 12/2009 | Zombo | F01D 5/288 702/34 |
| 2010/0176895 A1 | * | 7/2010 | Schmidhammer | H03J 3/185 333/32 |
| 2010/0246332 A1 | | 9/2010 | Huang | |
| 2010/0288323 A1 | | 11/2010 | Schroeder et al. | |
| 2011/0142091 A1 | | 6/2011 | Wardle et al. | |
| 2011/0233190 A1 | * | 9/2011 | Kukino | B28B 11/242 219/542 |
| 2013/0314765 A1 | | 11/2013 | Padilla et al. | |
| 2015/0124934 A1 | | 5/2015 | Gupta et al. | |
| 2015/0268152 A1 | | 9/2015 | Friedersdorf et al. | |
| 2016/0009602 A1 | * | 1/2016 | Brun | B32B 18/00 156/89.26 |
| 2016/0144452 A1 | | 5/2016 | Liou et al. | |
| 2016/0158841 A1 | | 6/2016 | Holcomb | |
| 2017/0356849 A1 | * | 12/2017 | Henderkott | G01N 21/643 |
| 2018/0120246 A1 | * | 5/2018 | Baucke | G01N 21/95 |
| 2019/0211704 A1 | * | 7/2019 | Whittle | F01D 5/284 |

FOREIGN PATENT DOCUMENTS

| | | | |
|---|---|---|---|
| JP | 409196887 A | * | 7/1997 |
| JP | 02006269336 A | * | 10/2006 |
| SU | 1394174 A | * | 4/1986 |
| SU | 1760478 A1 | * | 9/1992 |

\* cited by examiner

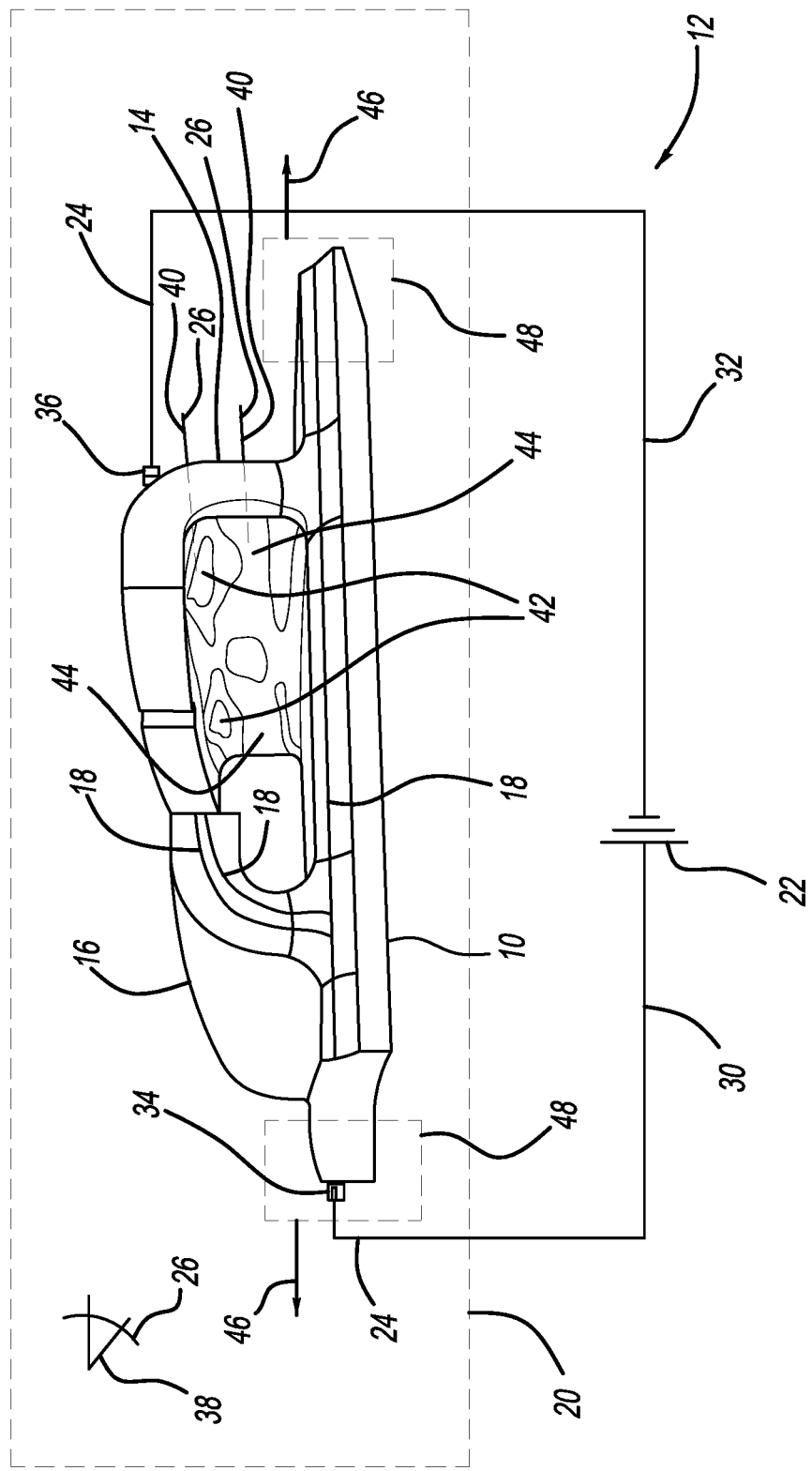

METHODS AND APPARATUSES FOR EVALUATING CERAMIC MATRIX COMPOSITE COMPONENTS

RELATED APPLICATION

The present disclosure claims the benefit of priority under 35 U.S.C. § 119(e) to U.S. Provisional Patent Application No. 62/369,780, filed on Aug. 2, 2016, which is hereby incorporated by reference in its entirety.

TECHNICAL FIELD

The present disclosure relates generally to ceramic matrix composite (CMC) components, and more particularly to methods and apparatuses for evaluating CMC components for detecting the presence of a defect.

BACKGROUND

Ceramic matrix composites (CMC) are used for making components for relatively high-strength, and high-temperature applications such as for various components in gas turbines and the like. The components may be fabricated by laminating multiple layers of ceramic fibers in a ceramic matrix to form a structure. In such constructions, the ceramic fibers effectively act as load bearing members and the ceramic matrix effectively acts as a load transferring mechanism for transferring the load between the load bearing members when the CMC component is stressed.

Given the high-strength, high-temperature applications for many CMC components, it is important that CMC components perform as intended to meet or exceed the requirements for these applications. Unfortunately, defects, such as cracks, discontinuities, voids, or porosity, in a CMC component can adversely affect its performance and further, such defects can be difficult to efficiently and timely detect. Accordingly, it is desirable to provide methods and apparatuses for evaluating CMC components to identify any defects in the structure. Moreover, it is desirable to provide methods and apparatuses for evaluating CMC components to monitor real-time initiation and growth of any defects in the structure while in service. Furthermore, other desirable features and characteristics of the present disclosure will become apparent from the subsequent detailed description and the appended claims, taken in conjunction with the accompanied drawings and this background.

BRIEF SUMMARY

Methods and apparatuses for evaluating ceramic matrix composite components are provided herein. In accordance with an exemplary embodiment, a method for evaluating a ceramic matrix composite (CMC) component includes applying an electrical voltage to the CMC component at conditions to heat and cause a temperature increase in at least a portion of the CMC component. The temperature increase is sensed for detecting a presence of a defect in the CMC component.

In accordance with another exemplary embodiment, a method for evaluating a CMC component is provided. The method includes providing the CMC component that includes a ceramic matrix reinforced with ceramic fibers and that has a defect portion and a non-defect portion. An electrical voltage is applied to the defect and non-defect portions of the CMC component at conditions to heat and cause a temperature increase in the defect portion relative to the non-defect portion. The temperature increase is sensed for detecting a presence of the defect portion of the CMC component.

In accordance with another exemplary embodiment, an apparatus for evaluating a CMC component is provided. The apparatus includes a power supply. An electrical connection arrangement is in communication with the power supply and is configured to operatively couple to the CMC component to apply an electrical voltage to at least a portion of the CMC component at conditions to heat and cause a temperature increase in the at least the portion of the CMC component. A temperature sensing arrangement is configured to sense the temperature increase for detecting a presence of a defect in the CMC component.

BRIEF DESCRIPTION OF THE DRAWINGS

The embodiments may be better understood with reference to the following drawings and description. The components in the figures are not necessarily to scale. Moreover, in the FIGURES, like-referenced numerals designate corresponding parts throughout the different views.

FIG. 1 is a perspective view of a ceramic matrix composite component and a schematic depiction of a method and apparatus for evaluating the ceramic matrix composite component in accordance with an exemplary embodiment.

DETAILED DESCRIPTION

The following detailed description is merely exemplary in nature and is not intended to limit the disclosure or the application and uses of the disclosure. Furthermore, there is no intention to be bound by any theory presented in the preceding background or the following detailed description.

Various embodiments contemplated herein relate to methods and apparatuses for evaluating CMC components. The exemplary embodiments taught herein apply an electrical voltage to the CMC component at conditions effective to heat and cause a temperature increase in at least a portion of the CMC component.

In one example, the electrical voltage is applied at two or more spaced apart points (e.g., locations or positions) on the CMC component so that electric current flows through the CMC component, thereby developing an electrical field. If any defects, e.g., porosity and/or delamination between the layers of the CMC component or the like, are present in one or more portions of the CMC component, the electrical resistance of the defect portion(s) relative to the adjacent non-defect portions is significantly greater. This leads to more localized electrical heating and higher temperatures at the defect portion(s) relative to the non-defect portions of the CMC component.

In an exemplary embodiment, the CMC component is monitored, e.g., real-time, by a temperature sensing arrangement that senses any temperature increases in the CMC component to identify the presence of any defects, e.g., defect portion(s), in the CMC component. In one example, the temperature sensing arrangement includes an infrared (IR) camera to monitor the component's temperature(s). In another example, the temperature sensing arrangement includes thermocouples that are operatively coupled to the CMC component to monitor the component's temperature(s).

It has been found that by using electrical current to heat the CMC component, while monitoring the component's temperature to identify any localized relative temperature increases, a relatively low cost, nondestructive evaluation (NDE) approach is provided for detecting the presence of one or more defects in the CMC component. Advantageously, this approach allows the CMC component to be inspected real-time and enhances the ability to nondestructively detect damage locations in, on, or along the CMC component in an efficient and timely manner.

FIG. 1 is a perspective view of a CMC component 10 and a schematic depiction of an apparatus 12 for evaluating the CMC component 10 in accordance with an exemplary embodiment. The CMC component 10 includes a CMC body 14. The CMC body 14 includes, consists of, or consists essentially of a ceramic matrix 16 reinforced with ceramic fibers 18.

In an exemplary embodiment, the CMC body 14 is formed of a porous ceramic preform that is filled, densified, and/or otherwise infiltrated with the continuous or substantially continuous ceramic matrix-forming material. The porous ceramic preform includes the ceramic fibers 18. The porous ceramic preform may be an arrangement of the ceramic fibers 18. The arrangement may be fixed in a desired shape.

In some examples, each of the ceramic fibers 18 may be a bundle and/or a tow of ceramic fibers. The fibers in each bundle or tow may be braided or otherwise arranged, for example in layers or the like.

The ceramic fibers 18 may include a material that is stable at temperatures above 1000 degrees Celsius (° C.). Examples of the ceramic fibers 18 may include fibers of alumina, mullite, silicon carbide, zirconia or carbon. The ceramic fibers 18 may not be organic or metallic fibers.

The ceramic matrix 16 of the CMC body 14 may include, for example, a silicon carbide ceramic matrix composite. The CMC body 14 may have various shapes or forms, not just the shape illustrated in FIG. 1.

Forming the CMC body 14 from the porous ceramic preform may include infiltrating a molten metal or alloy (for example, a silicon metal or alloy) into the porous ceramic preform. The molten metal or alloy is then solidified, for example, via cooling, sintering, and/or the like to form the ceramic matrix 16. In one example, the silicon metal or alloy fills the gaps, pores, and/or voids between the ceramic fibers of the porous ceramic preform to form a continuous or substantially continuous ceramic matrix 16 that is reinforced with the ceramic preform. The silicon metal or alloy may also react with a reactive element source present in the ceramic preform to form additional silicon based ceramic matrix material. In some examples, a chemical vapor infiltration coating may be applied to the porous ceramic preform prior to the melt infiltration to stiffen the ceramic fibers 18. Alternatively or in addition, forming the CMC body 14 from the porous ceramic preform may include chemical vapor infiltrating the porous ceramic preform instead of melt infiltrating a material into the porous ceramic preform.

The CMC component 10 may be a component of a gas turbine engine 20 such as forming at least part of a seal segment, a combustion liner, a turbine blade, a turbine vane, or another other part(s) that may be subjected to intense heat and/or pressure. In an exemplary embodiment and as illustrated, the CMC component 10 forms at least part of a seal segment of the gas turbine engine 20.

In an exemplary embodiment, the apparatus 12 includes a power supply 22 for providing electrical power, an electrical connection arrangement 24 that is in communication with the power supply 22 and is configured to operatively couple to the CMC component 10 to apply an electrical voltage. The apparatus 12 also includes a temperature sensing arrangement 26 for monitoring or otherwise sensing the temperature(s) of the CMC component 10.

As illustrated, the electrical connection arrangement 24 includes conductive lines 30 and 32 that pass electrical current from the power supply 22 to probes 34 and 36, respectively. The probes 34 and 36 are operatively coupled to the CMC component 10 at spaced apart discrete locations to apply an electrical voltage. As will be discussed in further detail below, the power supply 22 and the electrical connection arrangement 24 are cooperatively configured to apply the electrical voltage to at least a portion of the CMC component 10 at conditions effective to heat and cause a temperature increase in at least the portion of the CMC component 10.

In an exemplary embodiment, the temperature sensing arrangement 26 includes an infrared camera 38 for monitoring and sensing the temperature of the CMC component 10. In another embodiment, the temperature sensing arrangement 26 includes thermocouples 40 that are operatively coupled to the CMC component 10 for monitoring and sensing the temperature of the component 10.

In an exemplary embodiment, the CMC component 10 is evaluated using the apparatus 12 for detecting the presence of any defects by applying an electrical voltage to the CMC component 10 via the probes 34 and 36 at conditions effective to heat and cause a temperature increase in any defect portions 42 (e.g., portion(s) containing any defects such as delamination, porosity, or the like) of the CMC component 10, if present, relative to the non-defect portion 44 (e.g., portion(s) containing no substantive defects that could otherwise detrimentally affect performance). In an exemplary embodiment, the conditions include applying an electrical voltage of from about 10 to about 240 V, for example about 80 to about 120 V, a current of about 10 to about 1000 A, for example about 20 to about 40 A, and/or for a time of from about 0.5 to about 10 minutes, for example about 1 to about 5 minutes, to the CMC component 10, depending on the volume, electrical resistance of the inspection zone and the electrical voltage and current applied to the zone.

In one example, the probes 34 and 36 are in communication with the power supply 22 and apply an electrical voltage to the CMC body 14 at conditions effective to cause a temperature increase of the defect portion 42 of at least about 10° C., such as from about 10 to about 40° C., relative to the non-defect portion 44 to facilitate identifying or detecting the location(s) of the defect portion(s) 42 on the CMC body 14. The temperature increase of the defect portion 42 relative to the non-defect portion 44 is defined by the temperature of the defect portion 42 less the temperature of the non-defect portion 44. In another example, the electrical voltage is applied to heat the defect and non-defect portions 42 and 44 to a steady-state heat condition for a given component geometry, applied voltage, and ambient environmental conditions for identifying or detecting the location of the defect portion 42. Alternatively, the electrical voltage may be applied to heat the defect and non-defect portions 42 and 44 to a transient heat condition while monitoring the temperature increase (e.g., real-time) to detect the location of the defect portion 42.

Optionally, in an exemplary embodiment, a load 46 is applied to the CMC component 10 and/or body 14 to define a loaded or stressed condition while the electrical voltage is applied by the apparatus 12. Applying the load 46 to the CMC component 10 helps increase, for example, matrix cracking and/or delamination, thereby increasing electrical resistance and leading to more heating and higher material temperatures at the defect location(s) to facilitate detection of the defect(s). In one example, the temperature increase or change can be correlated to the applied stress to develop a relationship between CMC damage and applied stress as a function of temperature increase for a given component geometry, applied voltage, and ambient environmental conditions.

In one embodiment, the apparatus 12 includes a fixture 48 for supporting and applying the load 46 to the CMC component 10. For example, the fixture 48 may be configured to deform the CMC component 10 to a predetermined strain and stress level(s) that correlates to the strain and stress level(s) experienced by the CMC component 10 during operation in its intended function, e.g., during operation in the gas turbine engine 20 or the like.

In an alternative embodiment, the CMC component 10 may be disposed in the gas turbine engine 20 while the electrical voltage is applied by the apparatus 12. In one example, the gas turbine engine 20 is operating to apply the load 46 to the CMC component 10 so that the component 10 is in the loaded condition while the electrical voltage is applied and the temperature increase is monitored.

As discussed above, the temperature increase of the defect portion 42 relative to the non-defect portion 44 of the CMC component 10, whether in the transient or steady-state heat condition or in the loaded or unloaded condition, is sensed by the temperature sensing arrangement 26 either real-time or after the voltage has been applied and/or electrical resistance heating has occurred. In one example, the temperature profile of the CMC component 10 is monitored using the infrared camera 38 to sense any temperature increases and detect any defects. Alternatively, the temperature profile of the CMC component 10 may be monitored using the thermocouples 40 or the like to sense any temperature increases and detect any defects.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

What is claimed is:

1. A method for evaluating a ceramic matrix composite (CMC) component, the method comprising:

applying an electrical voltage to a CMC component at two or more spaced apart points on the CMC component so that electrical current flows through the CMC component, the CMC component comprising a CMC body including a ceramic matrix reinforced with ceramic fibers, thereby heating and causing a temperature increase in at least a portion of the CMC component; and sensing the temperature increase for detecting a presence of a defect in the CMC component, wherein the CMC component is a component for a gas turbine engine.

2. The method of claim 1, wherein applying the electrical voltage comprises applying a voltage of from about 10 to about 240 V.

3. The method of claim 1, wherein the electrical current is from about 10 to about 1000 A.

4. The method of claim 1, wherein the electrical voltage is applied for a time of from about 0.5 to about 10 minutes.

5. The method of claim 1, wherein applying the electrical voltage comprises heating the at least the portion of the CMC component to a transient heat condition, and wherein sensing the temperature increase comprises sensing the temperature increase of the at least the portion of the CMC component during the transient heat condition.

6. The method of claim 1, wherein applying the electrical voltage comprises heating the at least the portion of the CMC component to a steady-state heat condition, and wherein sensing the temperature increase comprises sensing the temperature increase of the at least the portion of the CMC component during the steady-state heat condition.

7. The method of claim 1, further comprising applying a load to the CMC component to define a loaded condition, and wherein applying the electrical voltage and sensing the temperature increase occur while the CMC component is in the loaded condition.

8. The method of claim 1, wherein applying the electrical voltage and sensing the temperature increase occur while the CMC component is disposed in the gas turbine engine.

9. The method of claim 8, wherein applying the electrical voltage and sensing the temperature increase occur while the gas turbine engine is operating.

10. The method of claim 1, wherein sensing the temperature increase comprises sensing the temperature increase of the at least the portion of the CMC component using an infrared camera.

11. The method of claim 1, wherein sensing the temperature increase comprises sensing the temperature increase of the at least the portion of the CMC component using one or more thermocouples.

12. The method of claim 1, further comprising supporting the CMC component with a fixture, and wherein applying the electrical voltage and sensing the temperature increase occur while supporting the CMC component by the fixture.

13. The method of claim 12, wherein the fixture is configured to apply a load to the CMC component, and wherein applying the electrical voltage and sensing the temperature increase occur while the load is applied to the CMC component.

* * * * *